United States Patent
Strickberger et al.

(10) Patent No.: US 6,852,082 B2
(45) Date of Patent: Feb. 8, 2005

(54) APPARATUS AND METHODS FOR PERFORMING NON-INVASIVE VASECTOMIES

(76) Inventors: Adam Strickberger, 1841 Cambridge, Ann Arbor, MI (US) 48104; Charles Cain, 4801 Starak La., Ann Arbor, MI (US) 48105; Matthew O'Donnell, 1607 Brooklyn, Ann Arbor, MI (US) 48104

( * ) Notice: Subject to any disclaimer, the term of this patent is extended or adjusted under 35 U.S.C. 154(b) by 234 days.

(21) Appl. No.: 10/198,429

(22) Filed: Jul. 17, 2002

(65) Prior Publication Data

US 2004/0015083 A1 Jan. 22, 2004

(51) Int. Cl.⁷ .................................................. A61B 8/14

(52) U.S. Cl. ...................................... 600/459; 128/842

(58) Field of Search .............................. 600/459, 417, 600/425, 437, 439, 462, 461, 463, 467; 128/842, 843

(56) References Cited

U.S. PATENT DOCUMENTS

| 4,269,174 | A | * | 5/1981 | Adair | 128/842 |
| 5,065,751 | A | * | 11/1991 | Wolf | 128/831 |
| 6,599,288 | B2 | * | 7/2003 | Maguire et al. | 606/27 |

* cited by examiner

*Primary Examiner*—Daniel I. Robinson
(74) *Attorney, Agent, or Firm*—Brinks Hofer Gilson & Lione (57) ABSTRACT

Apparatuses and methods for performing non-invasive vasectomies are provided. In a preferred embodiment, an apparatus according to the present invention comprises a main body defining a recess and an ultrasonic transducer disposed adjacent said recess and adapted to emit ultrasonic energy into said recess. A tissue clamp is removeably disposed in the recess and is adapted to receive parallel sections of a scrotum that include a portion of the vas deferens. The clamp is further adapted to position the vas deferens within an effective distance of the ultrasonic transducer. Also, the apparatus includes means for retaining the parallel sections and the vas deferens within the clamp during a procedure.

10 Claims, 6 Drawing Sheets

APPARATUS AND METHODS FOR PERFORMING NON-INVASIVE VASECTOMIES

FIELD OF THE INVENTION

The present invention relates to medical apparatuses and devices for use in vasectomy procedures. More specifically, the present invention relates to apparatuses and devices that facilitate the performance of non-invasive vasectomies. Also, the present invention relates to methods of performing vasectomy procedures in a non-invasive manner.

BACKGROUND OF THE INVENTION

Medical sterilizations are frequently performed on individuals to prevent unintended pregnancies. There are a variety of medical procedures that can be conducted to sterilize an individual, and both males and females can undergo the process. For either sex, and in all of the various procedures, a sexual organ of the individual is disrupted to prevent sexual reproductive processes in the individual. Based solely on anatomical considerations, male sterilization procedures are preferred due to the relatively superficial location of the vas deferens, the vessels that allow sperm to leave the epididymis and enter the ejaculatory duct. In some countries, however, social and political pressures override these anatomical concerns, and female sterilizations are more prevalent than procedures on males.

In the United States and other developed countries, the vasectomy, a medical procedure in which the vas deferens vessel is disrupted, has become the prominent sterilization procedure. As a result of this disruption, the ejaculation of sperm is prevented and the male is therefore effectively sterilized. The male remains otherwise sexually functional following the procedure.

There are currently two predominant methods of performing vasectomy procedures: the scalpel/incision method, and the no-scalpel method. In a conventional scalpel/incision vasectomy procedure, a scalpel is used to make two incisions in the scrotum to expose the vas deferens. Once the vessel is exposed, mechanical disruption of the vessel is performed. The disruption can be accomplished by various techniques, such as suture closures and cauterization. The need for incisions with this procedure make it somewhat undesirable for various reasons. For example, making incisions in the scrotum of a patient instills apprehension in many male patients, and likely serves as a reason for avoiding the procedure. Furthermore, the use of incisions generally necessitates the need for a local anesthetic, which may require an injection that can be equally as intimidating. Also, the incisions can lead to excessive bleeding, a relatively long healing time, and an increased possibility of post-procedure infection. Lastly, to complete the procedure, a physician must use stitches to close the incisions, which requires valuable physician time and may result in less comfort to the patient following the procedure.

The no-scalpel method of performing a vasectomy represents an improvement over the conventional scalpel/incision method because no incision is made and no stitches are required. Rather, in this procedure, a blunt puncture in the scrotum is made with a non-cutting blunt probe that teases the tissue apart. The puncture opening is stretched so that the vas deferens can be accessed. Next, the vas deferens is disrupted by the same techniques as those in the conventional method, such as suture closures and cauterization. Following disruption, the small puncture is able to close without requiring stitches. Therefore, bleeding and possibility of infection are reduced, but still remain. Although this technique represents an improvement over the scalpel/incision technique, it still constitutes an invasive procedure.

Considering the state of the prior art, a need exists for a non-invasive method of performing a vasectomy. Also, a need exists for novel medical apparatuses and devices that facilitate such non-invasive methods.

SUMMARY OF THE INVENTION

The present invention provides medical apparatuses and devices, as well as methods, that cure the defects of the prior art and satisfy the identified needs.

Accordingly, the present invention provides a medical device that facilitates non-invasive disruption of the vas deferens. The medical device includes a clamp adapted to maintain a section of the scrotum that includes a portion of the vas deferens in a position accessible by one or more ultrasonic transducers. In a preferred embodiment, the clamp comprises a body defining a throat region that is adapted to receive parallel sections of a scrotum that include a portion of the vas deferens. Also, the clamp includes means for retaining the parallel sections within the throat region. The clamp can also include means for delivering an anesthetic to the parallel sections, such as a textile material impregnated with a liquid anesthetic.

The present invention also provides a medical apparatus for performing non-invasive vasectomies using ultrasound. This apparatus receives a clamp according to the present invention in a manner that positions the vas deferens in proximity to one or more ultrasonic transducers. The transducers are used for therapy, i.e., disruption of the vas deferens, as well as diagnosis, i.e., verification of positioning and disruption of the vas deferens. In a preferred embodiment, the apparatus comprises a main body that defines a recess and a first ultrasonic transducer disposed adjacent the recess. A clamp according to the present invention is removeably disposed in the recess and is adapted to position parallel sections of a scrotum that include the vas deferens within an effective distance of the ultrasonic transducer. The apparatus further includes means for retaining the parallel sections and the portion of the vas deferens within a throat region of the clamp. The ultrasonic transducer is adapted to emit ultrasonic energy into the recess, and ultimately toward the vas deferens.

Lastly, the present invention provides methods of performing vasectomy procedures in a non-invasive manner. The methods according to the present invention utilize ultrasound to disrupt a portion of the vas deferens. Also, the methods can include the use of ultrasound to verify positioning of the vas deferens prior to disruption, as well as verification of the disruption following the procedure. In one preferred embodiment, a method according to the present invention comprises providing a medical apparatus, placing parallel sections of a scrotum that contain a portion of a vas deferens within a throat region of a clamp removeably received by the apparatus, activating means for retaining the parallel sections within the throat region, verifying the position of the portion of the vas deferens relative to an ultrasonic transducer of the apparatus, and energizing the ultrasonic transducer such that ultrasonic energy is delivered to the portion of the vas deferens. The method may further include verifying disruption of the portion of the vas deferens by viewing an image of the portion that is based on ultrasonic energy delivered to the vas deferens.

DETAILED DESCRIPTION OF PREFERRED EMBODIMENTS OF THE PRESENT INVENTION

While the invention is defined by the claims appended hereto, a more complete understanding of the invention can be obtained by referencing the following detailed description of preferred embodiments and the accompanying drawings. The following description of preferred embodiments of the invention provides examples of the present invention. The embodiments discussed herein are merely exemplary in nature, and are not intended to limit the scope of the invention in any manner. Rather, the description of these preferred embodiments serves to enable a person of ordinary skill in the relevant art to make and use the present invention.

Figure 1:
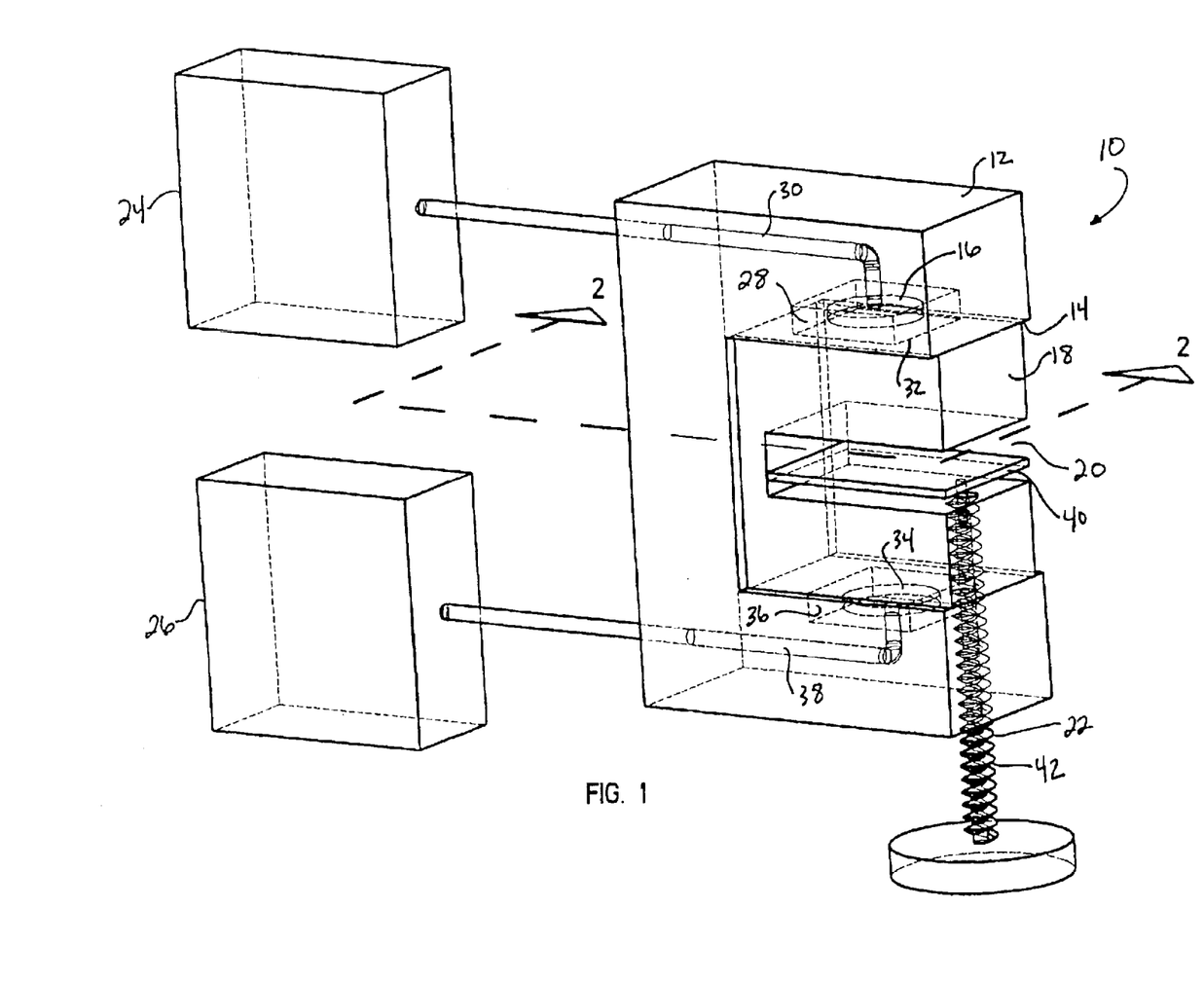
FIG. 1 is a perspective view of a medical apparatus according to a first preferred embodiment of the present invention.
Figure 2:
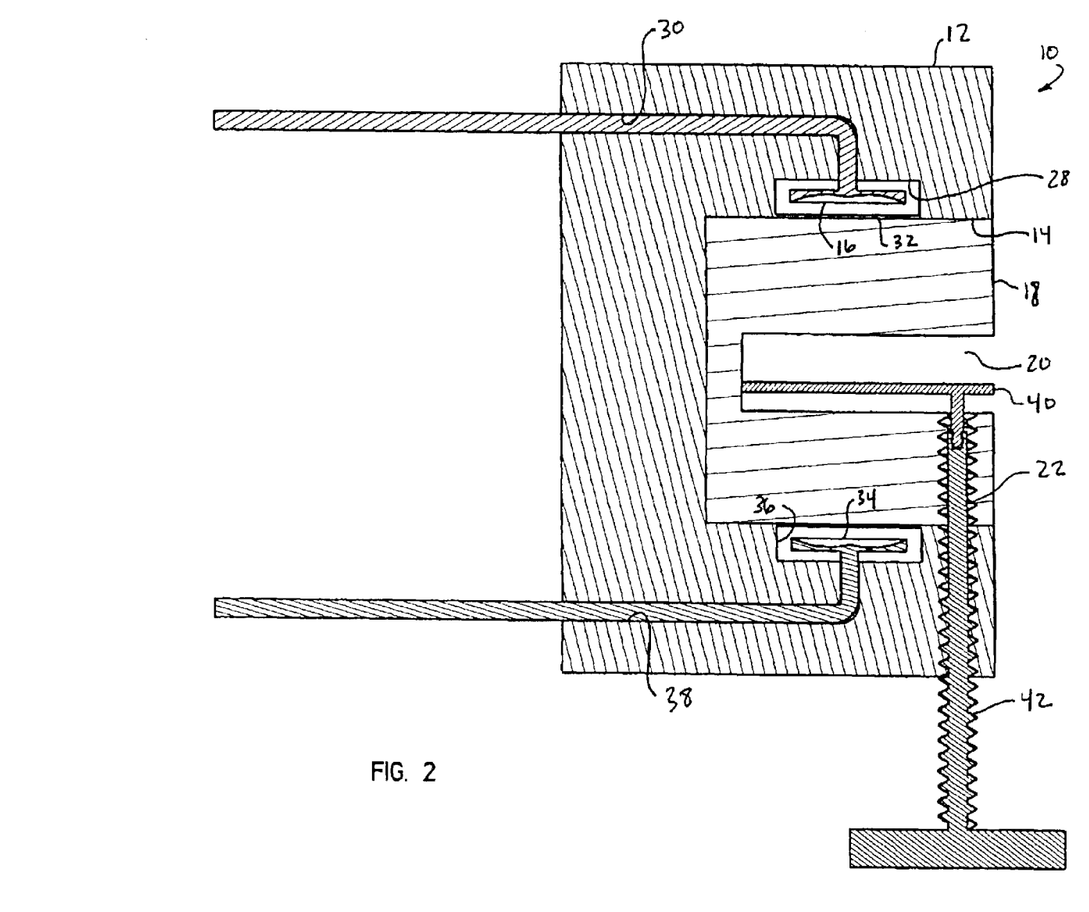
FIG. 2 is a cross-sectional view taken along line 2—2 in FIG. 1.

FIGS. 1 and 2 illustrate a medical apparatus according to a first preferred embodiment of the present invention. The medical apparatus is generally referred to in the Figures at reference number 10. The apparatus 10 includes a main body 12 that defines a recess 14. The apparatus 10 also includes a first ultrasonic transducer 16 that is disposed adjacent the recess 14. A tissue clamp 18 is removeably disposed in the recess 14 and defines a throat region 20 that is adapted to receive parallel sections of a scrotum of an individual that is undergoing a vasectomy. The parallel sections are manipulated by a caregiver to include the portion of the vas deferens that will be disrupted during the procedure. The tissue clamp 18 is adapted to position the portion of the vas deferens that will be disrupted within an effective distance of the first ultrasonic transducer 16, as will be describe more fully below. The apparatus 10 further includes means for retaining 22 the parallel sections and the portion of the vas deferens within the throat region 20 of the tissue clamp 18. Also, the apparatus 10 includes electronics appropriate for the transducer 16. Accordingly, as illustrated in FIG. 1, the apparatus 10 includes a first set of conventional transmission and receiving electronics 24, and can include a second set of transmission and receiving electronics 26 if a second ultrasonic transducer is utilized, as will be described more fully below. Furthermore, because the second transducer is preferably suited for generating images, as described below, the second set of electronics 26 preferably include conventional ultrasonic image generation and display electronics.

As illustrated best in FIG. 2, the main body preferably defines a C-shape with the recess 14 disposed centrally within the body 12. The main body 12 can be composed of any suitable material, and preferably is composed of material that prevents the transmission of ultrasonic energy. As best illustrated in FIG. 2, the main body 12 defines a cavity 28 for housing the first ultrasonic transducer 16, and also defines a passageway 30 for housing an appropriate connection between the transducer 16 and the electronics 24. Adjacent the cavity 28 and between the transducer 16 and tissue clamp 18, a window 32 is positioned and allows the transmission of ultrasonic energy from the transducer 16 toward the clamp 18 and throat region 20. The window 32 can simply comprise an opening in the main body 12, or may comprise a structural member such as a thin film of material such as a section of material that will allow the desired transmission of ultrasonic energy.

As illustrated in FIG. 2, if a second transducer 34 is present, a second cavity 36 and second passageway 38 are also present. The second cavity 36 and second passageway 38 are preferably similar to the first cavity 28 and first passageway 30, respectively.

The ultrasonic transducer 16 is preferably a conventional ultrasonic transducer known to those skilled in the art. The apparatus 10 according to the present invention must include at least the first ultrasonic transducer 16, which is adapted to emit ultrasonic energy sufficient to disrupt a portion of the vas deferens. Accordingly, the first ultrasonic transducer preferably is adapted to emit ultrasonic energy having a wavelength of between 1 and 20 mhz. The apparatus 10 may further include a second ultrasonic transducer 34. In a preferred embodiment, the second ultrasonic transducer 34 is adapted to emit ultrasonic energy sufficient to generate an image of the portion of the vas deferens, which can be used to verify location of the vas deferens and/or disruption of the vas deferens, as discussed below. If the second ultrasonic transducer 34 is present, the second ultrasonic transducer 34 is preferably adapted to emit ultrasonic energy having a wavelength between 5 and 30 mhz. Both ultrasonic transducers 16, 34 are adapted to emit ultrasonic energy into the recess 14 of the main body 12 and toward the tissue clamp 18. Ultimately, of course, the ultrasonic energy reaches the parallel scrotum sections and vas deferens contained within the throat region 20 of the tissue clamp 18 during a procedure utilizing the apparatus 10.

The tissue clamp 18 of the present invention receives the parallel sections of scrotum that contain the vas deferens and maintain the sections in the vas deferens in a substantially constant position during a procedure. Accordingly, the tissue clamp 18 defines a throat region 20 that is able to receive these parallel sections of scrotum. Also, the tissue clamp 18 preferably is a separate article from the main body 12 of the apparatus, and is adapted to be removeably received into the recess 14 of the main body 12. This modular design allows the tissue clamp 18 to be used as a consumable item while the main body 12, which contains some of the relatively expensive components of the apparatus 10, can be used as a relatively long-term piece of equipment.

Because the tissue clamp 18 is positioned adjacent the transducer 16, 34, the tissue clamp 18 must allow for the transmission of ultrasonic energy toward the throat region 20. Accordingly, the tissue clamp 18 is preferably formed of acoustically transparent material.

To assure a substantially constant positioning of the scrotum sections and vas deferens during a procedure, the apparatus 10 includes means for retaining 22. The means for retaining 22 can comprise any suitable means for retaining a section of tissue within the throat region 20. In the preferred embodiment, illustrated in FIGS. 1 and 2, the means for retaining 22 comprise a moveable surface 40 that is disposed within the recess 14. The moveable surface 40 is connected to a driving member 42 that is adapted to affect movement of the moveable surface 40. By activating the driving member 42, the moveable surface 40 is moved within the throat region 20 such that the effective width of the throat region 20 is lessened, ultimately to a point that allows the scrotum sections and vas deferens to be clamped within the throat region 20 by force between the moveable surface 40 and the tissue clamp 18. A best illustrated in FIG. 2, the driving member 42 preferably extends through the main body 12 of the apparatus 10 and into the tissue clamp 18. The driving member 42 is preferably associated with the main body 12 while the moveable surface 40 is preferably associated with the tissue clamp 18. When a new tissue clamp 18 is positioned within the recess 14 of the main body 12, in preparation for a procedure, the driving member 42 is moved toward the moveable surface 40 until a suitable engaging connection is achieved between a driving member 42 and moveable surface 40. At this point, the driving member 42 can be used to affect movement of the moveable surface 40, allowing effective retaining of the scrotum sections and vas deferens within the throat region 20 of the tissue clamp 18.

Figure 3:
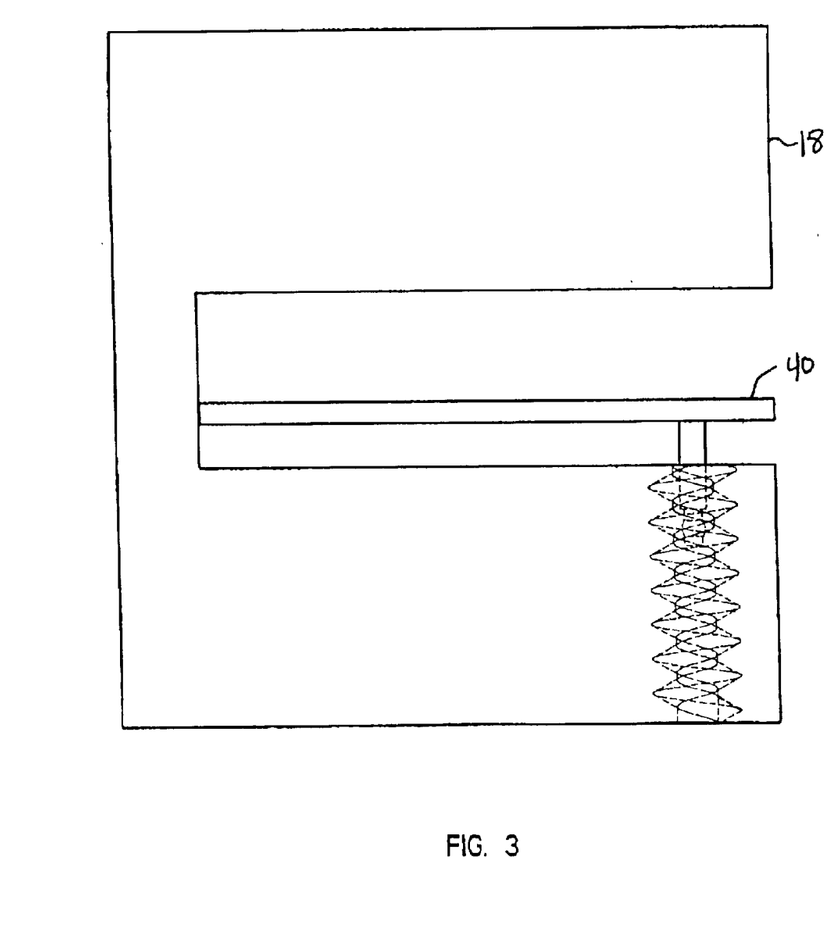
FIG. 3 is a side view of a tissue clamp according to a preferred embodiment of the present invention.

FIG. 3 illustrated the tissue clamp 18 separate and distinct from the main body of the apparatus. This demonstrates the modular structure of the apparatus 10, and highlights the use of the tissue clamp 18 as a consumable item. It is envisioned that numerous identical tissue clamps 18 would be utilized with a single main body. In this preferred embodiment, the tissue clamp 18 includes the moveable surface 40.

Figure 4:
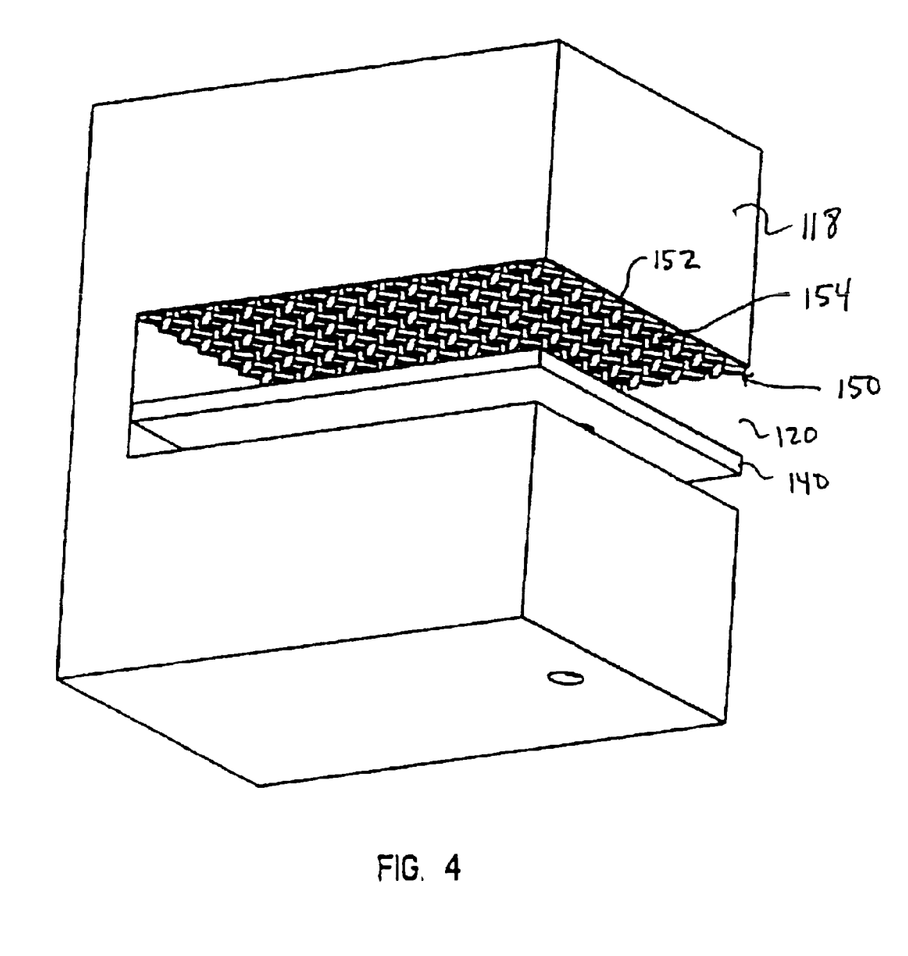
FIG. 4 is a perspective view of a tissue clamp according to another preferred embodiment of the present invention.

FIG. 4 illustrates a tissue clamp 118 according to another preferred embodiment of the present invention. In this embodiment, the tissue clamp 118 includes a moveable surface 140, as well as a means for delivering 150 an anesthetic. Any suitable means for delivering an appropriate anesthetic to the scrotum sections can be utilized. As illustrated in the Figure, the means 150 preferably comprise a substrate 152, such as a textile pad, disposed on an inner surface of the throat region 120 and impregnated with a suitable anesthetic 154, such as a liquid contact or topical anesthetic.

Figure 5:
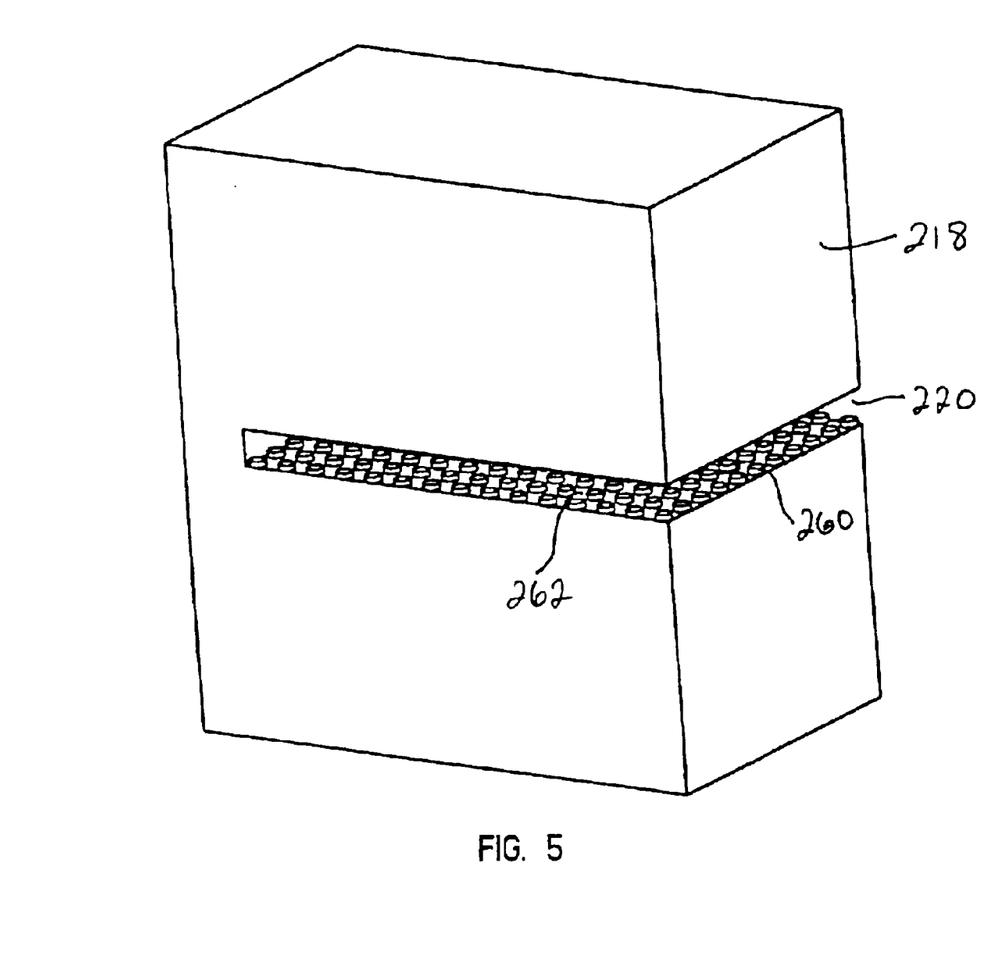
FIG. 5 is a perspective view of a tissue clamp according to another preferred embodiment of the present invention.

FIG. 5 illustrates a tissue clamp 218 according to another preferred embodiment of the present invention. In this embodiment, the tissue clamp 218 defines a throat region 220 similar to the preferred embodiments discussed above. In this embodiment, however, the throat region 220 is relatively narrow compared to the throat regions of the previous embodiments. The width of the throat region 220 in this embodiment is preferably sufficient to allow the parallel scrotum sections to be received into the throat region 220. In this embodiment, the means for retaining 222 the sections within the throat region 220 do not comprise a driving member and moveable surface, as in the previous embodiments. In this embodiment, an adhesive layer 260 is disposed on an inner surface 262 of the throat region 220. The adhesive layer 260 preferably comprises a monolayer of adhesive suitable for use with human tissue, and preferably is able to retain the scrotum sections within the throat region 220 following an application of a small amount of force against the adhesive layer 260. Particularly preferable, the adhesive layer 260 comprises an adhesive that can retain the parallel sections upon contact, and is able to release the parallel sections with minimal discomfort.

Figure 6:
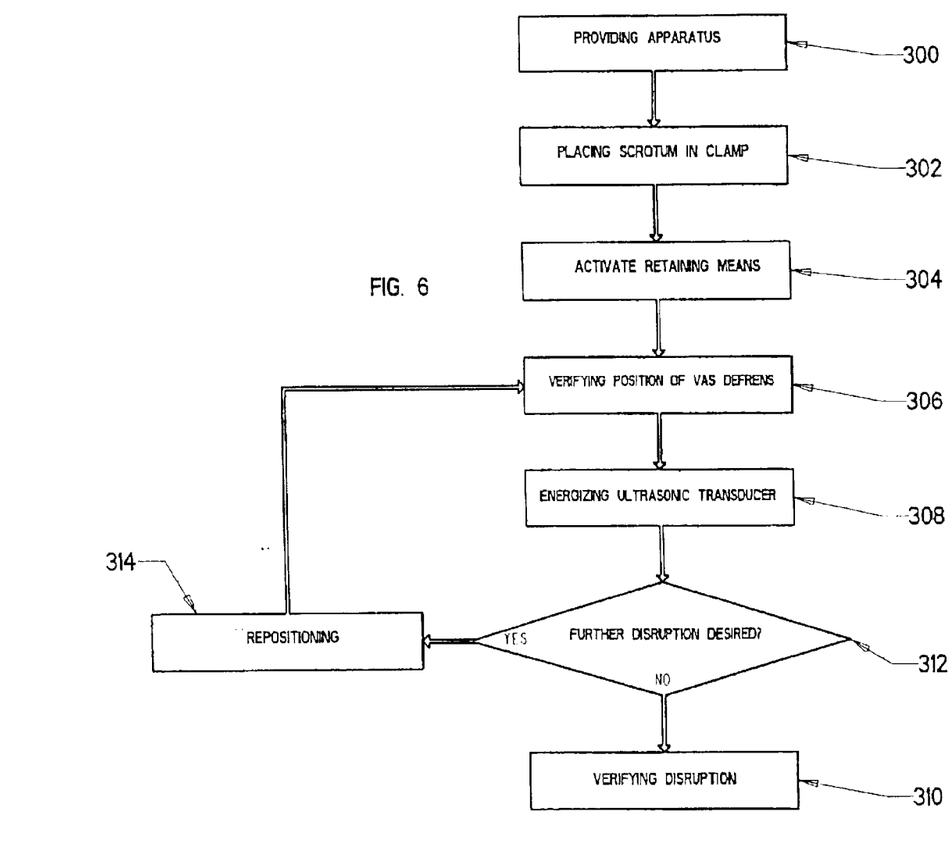
FIG. 6 is a flow diagram of a preferred method according to the present invention.

The present invention also provides methods of performing noninvasive vasectomies. FIG. 6 is a flow chart illustrating steps involved in a preferred method of the present invention. As illustrated in the Figure, the preferred method includes providing an apparatus 300 according to the present invention. Accordingly, this step preferably comprises providing an apparatus that comprises a main body defining a recess, a first ultrasonic transducer disposed adjacent the recess and adapted to emit ultrasonic energy into the recess, a tissue clamp that is removeably disposed in the recess and that defines a throat region adapted to receive parallel sections of a scrotum that include a portion of a vas deferens.

The tissue clamp is adapted to position the vas deferens portion within an effective distance of the first ultrasonic transducer. Also, the apparatus preferably includes means for retaining the parallel sections and the portion of the vas deferens within the throat region of the tissue clamp.

In a further step 302, the method includes placing the scrotum sections in the tissue clamp of the apparatus. In a further step 304, the method includes activating the retaining means of the apparatus. In this step, the means for retaining the parallel sections and the portion of the vas deferens within the throat region of the tissue clamp are activated to maintain the parallel sections and the vas deferens in a substantially constant position relative to the ultrasonic transducer of the apparatus.

In a further step 306, the position of the vas deferens relative to the ultrasonic transducer can be verified. In a preferred method, the verifying of the position comprises viewing an image based on ultrasonic energy delivered to the portion of the vas deferens that is within the throat region of the tissue clamp. Particularly preferably, this step involves viewing an image generated by a second ultrasonic transducer that is included in the apparatus utilized in the method.

In a further step 308, the method includes energizing an ultrasonic transducer of the apparatus. In this step, the ultrasonic transducer is energized such that ultrasonic energy is emitted and directed toward the parallel sections and vas deferens within the throat region of the tissue clamp. The ultrasonic energy is preferably sufficient to disrupt the portion of the vas deferens that is within the throat region. Accordingly, the ultrasonic energy preferably has a wavelength between 1 and 20 mhz.

In a further step 310, the method may include verifying the disruption of the vas deferens. In this step, the verifying can again be accomplished by viewing an image of the portion of vas deferens. Preferably, the image is based on ultrasonic energy delivered to the vas deferens by a second, diagnostic ultrasonic transducer.

Multiple disruptions of the vas deferens may be desired in a procedure conducted according to methods of the present invention. Accordingly, the methods of the present invention allow for multiple disruptions. Thus, in a further step 312, if multiple disruptions are desired, a repositioning step 314 is followed. In this step 314, the scrotum sections and/or the vas deferens are repositioned within the throat region of the tissue clamp such that a new portion of the vas deferens, i.e., a portion substantially left in tact following the first disruption, is positioned within an effective distance of the ultrasonic transducer of the apparatus. If the apparatus includes means for retaining the scrotum sections and vas deferens within the throat region, the retaining means can be deactivated prior to the repositioning, and reactivated following the repositioning. Following the repositioning, the position of the vas deferens can again be verified in the verifying step 306. Then, the energizing step 308 is again conducted. This loop of deciding 312 whether further disruptions are desired, repositioning 314 and re-energizing 308, with optional verifying 306, can be conducted multiple times, and the number of cycles will depend on the number of disruptions that is desired.

Lastly, the method can include verifying 310 the disruption of the vas deferens. Preferably, the verifying 314 is conducted in a similar manner as the verifying of the position of the vas deferens 306. Thus, the verifying of the disruption 314 preferably comprises viewing an image of the disrupted portion of the vas deferens that is based on ultrasonic energy that was delivered to the portion of the vas deferens. Particularly preferably, the image is based upon ultrasonic energy delivered to the portion of the vas deferens from a second ultrasonic transducer, such as a diagnostic ultrasonic transducer.

The foregoing disclosure includes the best mode devised by the inventor for practicing the invention. It is apparent, however, that several variations in the present invention may be conceivable by one skilled in the art. Inasmuch as the foregoing disclosure is intended to enable one skilled in the pertinent art to practice the instant invention, it should not be construed to be limited thereby, but should be construed to include such aforementioned variations.

What is claimed is:

1. A medical apparatus for disrupting a portion of a vas deferens of an individual, the apparatus comprising:
    a main body defining a recess;
    a first ultrasonic transducer disposed adjacent said recess and adapted to emit ultrasonic energy into said recess;
    a tissue clamp removeably disposed in said recess and defining a throat region adapted to receive parallel sections of a scrotum of the individual that include the portion of the vas deferens, said tissue clamp adapted to position the portion of the vas deferens within an effective distance of said first ultrasonic transducer; and
    means for retaining the parallel sections and the portion of the vas deferens within said throat region.

2. The medical apparatus of claim 1, further comprising a second ultrasonic transducer disposed adjacent said recess and adapted to emit ultrasonic energy into said recess.

3. The medical apparatus of claim 2, wherein said first ultrasonic transducer is adapted to emit ultrasonic energy sufficient to disrupt the portion of the vas deferens; and
    wherein said second ultrasonic transducer is adapted to emit ultrasonic energy sufficient to generate an image of the portion of the vas deferens.

4. The medical apparatus of claim 3, wherein said first ultrasonic transducer is adapted to emit ultrasonic energy having a wavelength between 1 and 20 MHz; and
    wherein said second ultrasonic transducer is adapted to emit ultrasonic energy having a wavelength between 5 and 30 MHz.

5. The medical apparatus of claim 1, further comprising means for delivering an anesthetic to the parallel sections.

6. The medical apparatus of claim 5, wherein the means for delivering an anesthetic comprise a substrate disposed within said throat region and containing said anesthetic.

7. The medical apparatus of claim 6, wherein said substrate comprises a textile and said anesthetic comprises a liquid.

8. The medical apparatus of claim 1, wherein said means for retaining comprise a moveable surface disposed within said recess and connected to a driving member adapted to effect movement of said moveable surface within said recess.

9. The medical apparatus of claim 8, wherein said driving member extends through said main body.

10. The medical apparatus of claim 1, wherein said throat region includes an inner surface; and
    wherein said means for retaining comprise an adhesive layer disposed on said inner surface.

* * * * *